US012263322B1

(12) United States Patent
Alroqi

(10) Patent No.: US 12,263,322 B1
(45) Date of Patent: Apr. 1, 2025

(54) EPISTAXIS CONTROLLING DEVICE AND METHOD OF USING THE SAME

(71) Applicant: KING SAUD UNIVERSITY, Riyadh (SA)

(72) Inventor: Ahmad Salman Alroqi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/638,167

(22) Filed: Apr. 17, 2024

(51) Int. Cl.
*A61M 31/00* (2006.01)
*A61B 17/28* (2006.01)

(52) U.S. Cl.
CPC ......... *A61M 31/00* (2013.01); *A61B 17/2812* (2013.01)

(58) Field of Classification Search
CPC . A61M 31/00; A61M 16/068; A61B 17/2812; A61B 17/02; A61B 17/24; A61B 17/242; A61B 2017/246
See application file for complete search history.

(56) References Cited

U.S. PATENT DOCUMENTS

| 4,457,756 | A | | 7/1984 | Kern | |
|---|---|---|---|---|---|
| 4,895,559 | A | | 1/1990 | Shippert | |
| 5,529,571 | A | * | 6/1996 | Daniel | A61B 17/0206 600/218 |
| D406,888 | S | | 3/1999 | Doyle | |

| 10,299,670 | B1 | * | 5/2019 | Sumaily | A61B 1/32 |
|---|---|---|---|---|---|
| 2017/0113330 | A1 | * | 4/2017 | Williams | B25B 7/18 |
| 2019/0167486 | A1 | | 6/2019 | Clayborne et al. | |

FOREIGN PATENT DOCUMENTS

| CN | 104758026 A | 7/2015 |
|---|---|---|
| CN | 111358524 A | 7/2020 |

OTHER PUBLICATIONS

Veluswamy et al., "Nasal Septal Clips: An Alternative to Nasal Packing After Septal Surgery?," Indian Journal of Otolaryngology and Head & Neck Surgery, 64(4): 346-350, Nov. 30, 2011.

* cited by examiner

*Primary Examiner* — Lauren P Farrar
(74) *Attorney, Agent, or Firm* — Nath, Goldberg & Meyer; Joshua B. Goldberg

(57) ABSTRACT

A medical apparatus for controlling or treating epistaxis includes a first elongated structural component, a second elongated structural component, and a coupling component pivotally coupling the first and second elongated structural components to one another. The first elongated structural component includes a first handle portion, a first operating portion and a first through opening disposed between the first handle portion and the first operating portion. The second elongated structural component includes a second handle portion, a second operating portion and a second through opening disposed between the second handle portion and the second operating portion. The coupling component extends in the first and second through openings. Each one of the first and second operating portions may include an elongated body with one or more slits extending therealong. Each slits defines a receiving area for one or more nasal packs.

18 Claims, 8 Drawing Sheets

EPISTAXIS CONTROLLING DEVICE AND METHOD OF USING THE SAME

TECHNICAL FIELD

The present disclosure relates to medicine, and more particularly, to an epistaxis controlling/treating device and a method of using the same.

DISCUSSION OF THE RELATED ART

Nosebleeds (or epistaxis, in medical terms) are a common presentation in health care facilities, affecting almost all age groups. Nosebleeds vary in severity, with the majority of the cases being mild and intermittent. Epistaxis can be classified as anterior epistaxis, when it originates from the front region of the nose, and posterior epistaxis, when it originates from the back region of the nose.

Anterior epistaxis can be managed in different ways, with preventative/treatment measures including trauma prevention, nasal dryness, nasal packing and cautery. In some cases, a patient suffering from anterior epistaxis might need more aggressive measures, including embolization or arterial ligation.

It is generally accepted that anterior epistaxis most commonly arises from an area of the nose called Little's area (or Kiesselbach's plexus). Little's area is an area of anastomosis between different arteries. One of the lines of treatment of epistaxis believed to originate from Little's area is the insertion of a nasal packing device (e.g., an elastic, inflatable tube-like device that may be referred to hereinafter as "nasal pack(s)" for brevity purposes) in each of the two nasal cavities. Each nasal pack may then be injected or irrigated with saline to become enlarged (e.g., to inflate, especially circumferentially). The enlargement of each nasal pack inside of its respective nasal cavity enables the devices to apply pressure on the bleeding site (e.g., to Little's area). The application of pressure to the bleeding site for a certain amount of time generally causes the bleeding to stop. The nasal packs may then be removed from the patient's nasal cavities.

A disadvantage of using nasal packs is that their enlargement inside of the nasal cavities fills the nasal cavities entirely (especially in cross-section), thereby preventing a patient from breathing through the nose.

SUMMARY

The present disclosure relates to a medical device configured to control and/or treat epistaxis, including epistaxis originating from Little's area, while enabling a patient to breathe through the nose during the control/treatment process. The medical device includes a pair of elongated structural components that are pivotally coupled to one another at a region along their respective lengths. This configuration defines a handle portion in each elongated structural component and an operating portion in each operating component. Each operating portion of the medical device may include one or more slits extending along a length of the operating portion. Each slit may be configured to receive a nasal pack therein.

Each slit of each operating portion of the medical device may be loaded with a nasal pack. One of the loaded operating portions may be inserted in a first nasal cavity of a user and the other loaded operating portion may be inserted in a second nasal cavity of a patient.

Upon insertion, the nasal pack(s) loaded in each operating portion of the medical device may be inflated with a liquid, for example, saline, to control and/or treat the epistaxis of the patient.

The configuration of each operating portion of the medical device may restrict radial (or lateral) expansion of the nasal packs along a portion of the periphery of each nasal pack. This configuration prevents total blockage of the patient's nasal cavities during the epistaxis control/treatment process, thereby enabling the patient to breathe through the nose while being treated for epistaxis.

BRIEF DESCRIPTION OF THE DRAWINGS

The above and other features of the present disclosure will become more apparent by describing in detail exemplary embodiments thereof in conjunction with the accompanying drawings, in which.

DETAILED DESCRIPTION OF THE EMBODIMENTS

Figure 1A:
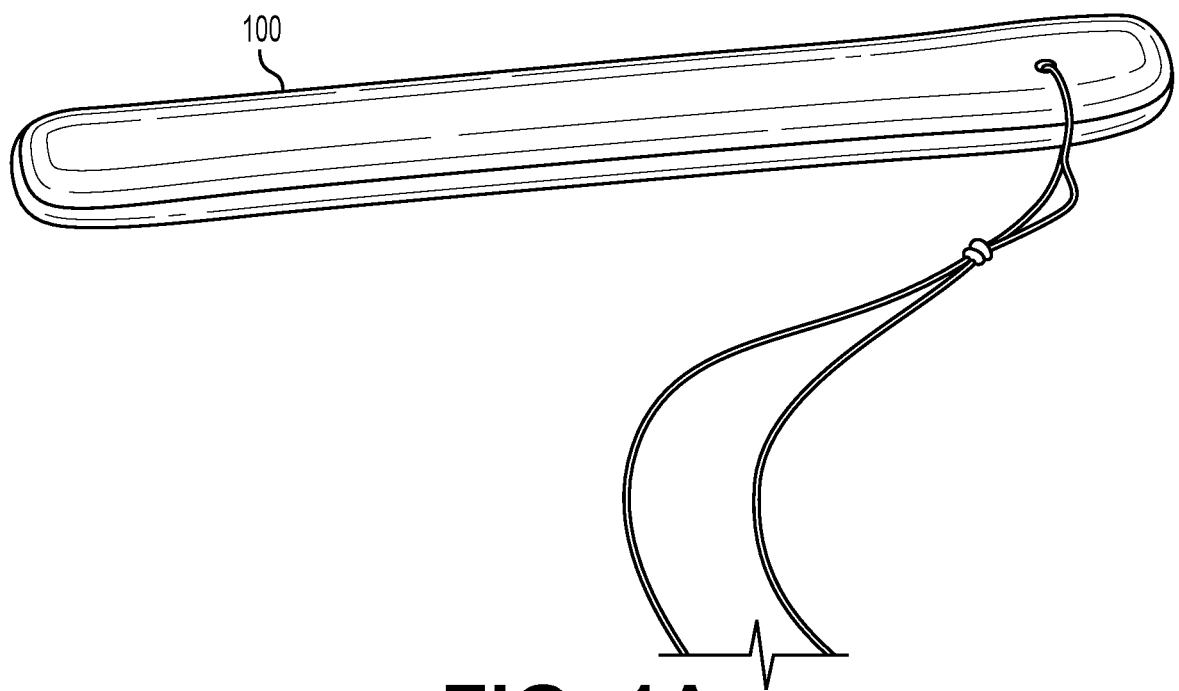
FIG. 1A is a perspective view illustrating a nasal pack in an uninflated state.

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein may also include the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Figure 1B:
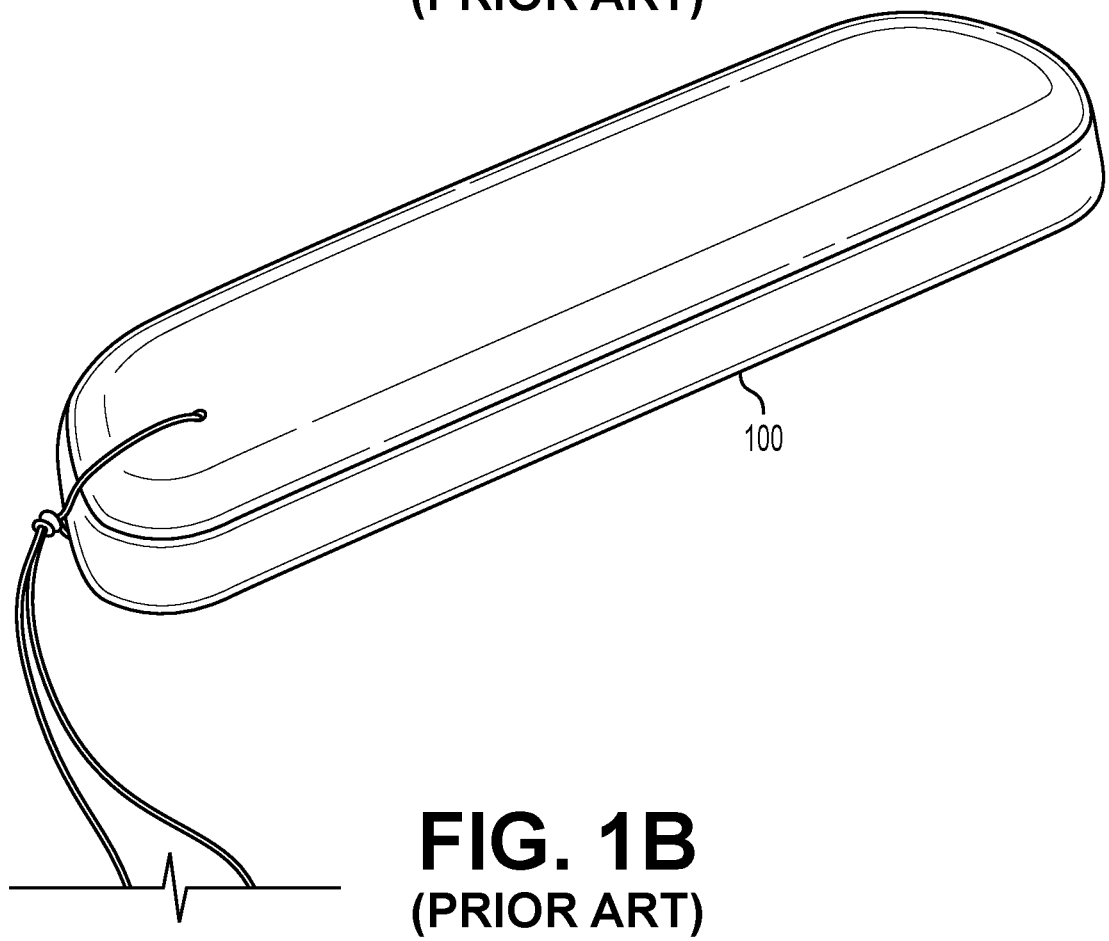
FIG. 1B is a perspective view illustrating the nasal pack of FIG. 1A in an inflated state.

FIGS. 1A-1B, respectively, illustrate a known type of nasal pack 100 in the uninflated and inflated states. As illustrated in FIG. 1A, the nasal pack 100 may have a flat bar shape in the uninflated state. The nasal pack 100 may be inflated, as illustrated in FIG. 1B, for example, by injecting it with a saline solution or by nasal irrigation when inserted in a nasal cavity.

Figure 2A:
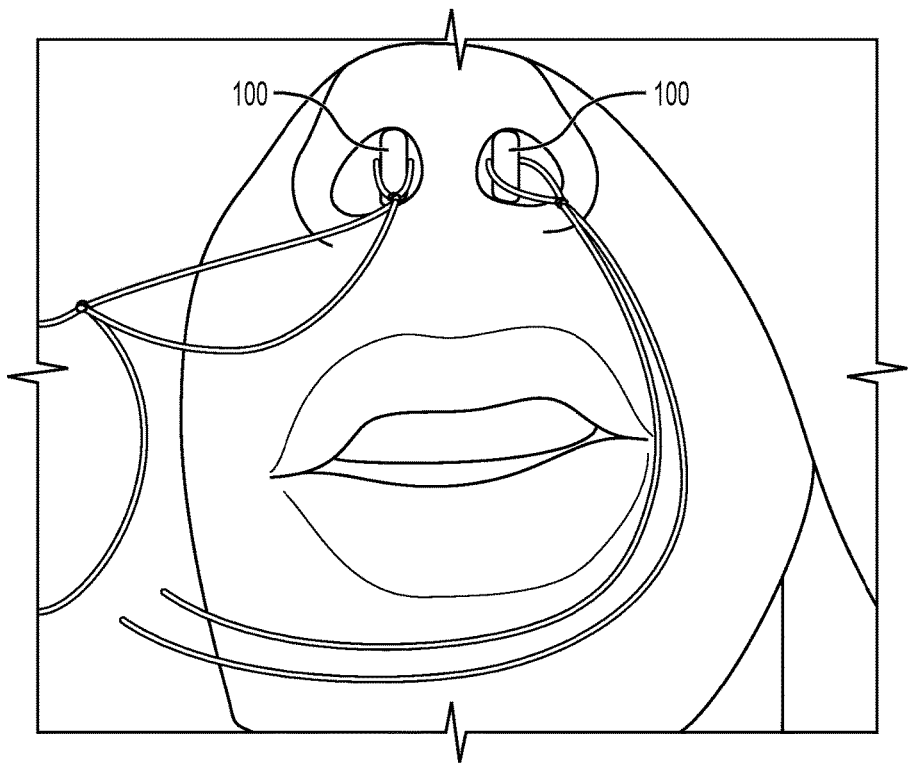
FIG. 2A is a perspective view illustrating a patient with a pair of uninflated nasal packs, as illustrated in FIG. 1A, inserted in the patient's nose.
Figure 2B:
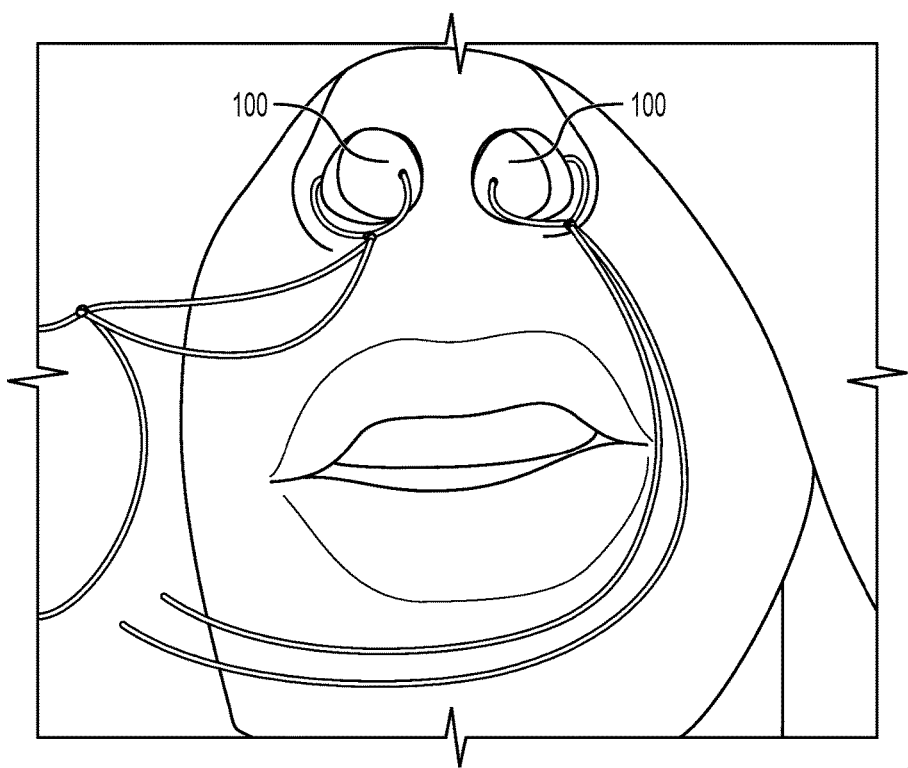
FIG. 2B is a perspective view illustrating the patient of FIG. 2A with the nasal packs in the inflated state.

When a patient suffers from epistaxis, a nasal pack 100 may be inserted in each nasal cavity of the patient in the deflated state, as illustrated in FIG. 2A. Each of the nasal packs 100 may then be inflated, as illustrated in FIG. 2B. The inflated nasal packs 100 apply pressure all-around the nasal cavity over a period of time in order to stop the bleeding.

The usage of nasal packs 100 in this manner is disadvantageous in that it substantially prevents the patient from breathing through the nose by virtue of blocking the entirety of the nasal cavities. In addition, the usage of nasal packs 100 as illustrated in FIGS. 2A-2B is disadvantageous because they apply an unnecessary and/or undue amount of pressure to the nasal floor and the inferior turbinate.

The present disclosure relates to a medical apparatus that is configured to control epistaxis in general, including anterior epistaxis, while enabling a patient to breathe through the nose when the medical device is inserted in the patient's nasal cavities to control/stop the bleeding.

More particularly, a medical device of the present disclosure is configured to be used in conjunction with nasal packs to apply pressure to the internal part of a patient's nose where the bleeding occurs (to control/stop the bleeding), while enabling the patient to breathe through the nose. This is so because the medical apparatus of the present disclosure is configured to direct the application of pressure, via the nasal packs, mainly to the bleeding site inside of the nose without blocking the entire nasal passageway. That is, the apparatus of the present disclosure is configured to prevent the nasal packs from applying pressure all-around inside of the nasal cavities to prevent the nasal packs from completely blocking the nasal cavities.

A medical apparatus of the present disclosure includes two elongated structural components that are pivotally connected to one another, for example, and in a non-limiting configuration, approximately at their respective mid-lengths. This configuration defines a handle portion of the device, by the halves of the elongated structural components extending on one side of the pivoting point, and an operating part of the device, by the halves of the elongated structural components extending on the other side of the pivoting point.

The parts of the elongated components defining the handle portion of the device may be referred to as handle components (with each individual one being referred to as a handle component). The parts of the elongated components defining the operating part of the device may be referred to as operating components (with each individual one being referred to as an operating component).

Each operating component may have an elongated body with at least one slit extending along its length. For convenience of explanation, the at least one slit may be referred to as "the slit." A nasal pack, in a deflated state, can be inserted in the slit of each of the two operating components. The operating components with a nasal pack inserted in their respective slits can be inserted in the nasal cavities of a patient (i.e., each operating component can be inserted in one of the two nasal cavities).

The nasal packs can then be inflated by being injected with saline or via nasal irrigation. The inflation of the nasal pack in each slit causes the nasal pack to expand (or protrude) outwardly from the slit, thereby applying pressure to a bleeding site in the nasal cavity to stop the bleeding. Simultaneously, the structure of each operating component that extends on either side of the slit restricts the expansion of the nasal packs outwardly (or laterally) through said structure due to the stiffness of the structure.

Since the size (e.g., the cross-sectional size) of each operating component of the device may be smaller than the size (e.g., the cross-sectional size) of the receiving nasal cavity in order to be comfortably inserted therethrough, an air gap may be formed inside each nasal cavity between the wall of the nasal cavity and the operating component of the device inserted in the cavity.

Moreover, since the structure of each operating component that covers the nasal pack on either side of the slit restricts (or resists) outwardly expansion of the nasal pack through said structure, the air gap may be maintained between each operating component and the wall of the nasal cavity that it is inserted in (i.e., the structure of each operating component prevents the nasal pack from freely expanding in the nasal cavity to block the entire cavity) when the nasal pack is inflated. The air gap extends along the length of each operating component. Therefore, the air gap defines an air passageway in each nasal cavity, enabling the patient to breathe through the nose while being treated for epistaxis.

Referring to FIGS. 4-8, a medical apparatus 1000 of the present disclosure includes a pair of elongated structural components 200, 400 (also referred to as first and second elongated structural components) that are pivotally connected to one another by a coupling component 300. Each one of the elongated structural components 200, 400 and the coupling component 300 may be made of a metal. Non-limiting examples of suitable metals include stainless steel (e.g., medical grade stainless steel), titanium, nickel, chromium, etc., or alloys thereof. The metal or alloy may feature, for example, a high resistance to corrosion, oxidation and/or staining for ease of cleaning or sterilization (without corroding/staining/rusting due to cleaning/sterilization and/or use) since the medical apparatus 1000 is contemplated to be used for medical purposes on humans. Alternatively, or in addition, each one of the elongated structural components 200, 400 and the coupling component 300 may include a polymeric material.

Figure 4:
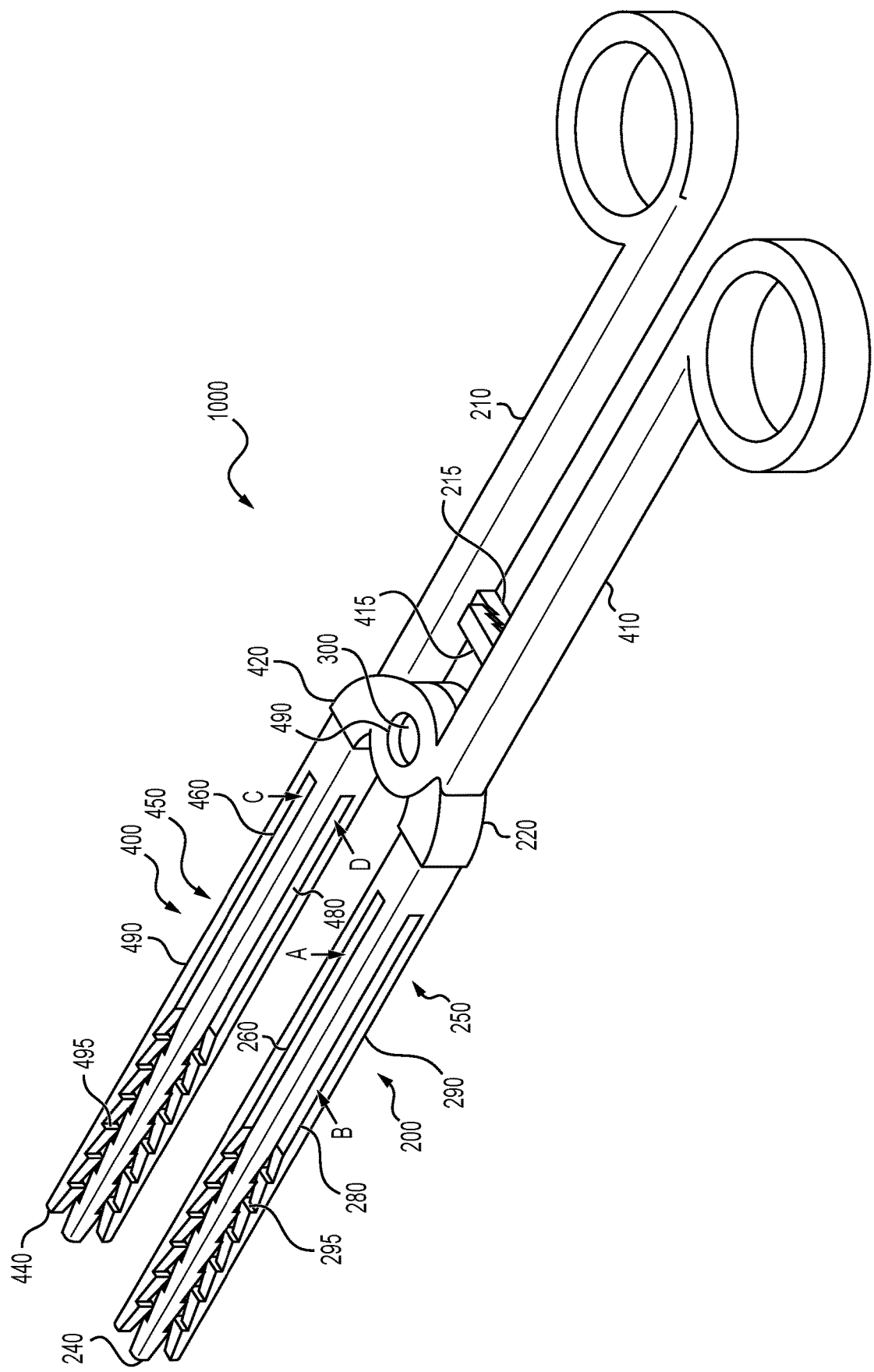
FIG. 4 is a perspective view illustrating a medical device, according to an embodiment of the present disclosure, configured to treat epistaxis.

As illustrated in FIG. 4, the first elongated structural component 200 may include a first handle portion 210, a first operating portion 250 and a through opening disposed between the first handle and operating portions 210, 250. The through opening of the first elongated structural component 200 is not visible in FIG. 4, but it is disposed under a through opening 490 of the second elongated structural component 400 when the apparatus 1000 is oriented as illustrated in FIG. 4.

Referring to FIG. 4, the second elongated structural component 400 may include a second handle portion 410, a second operating portion 450 and the through opening 490 disposed between the second handle portion 410 and the second operating portion 450.

The coupling component 300 may extend at least partially through the through opening of the first elongated structural component 200 and through the through opening 490 of the second elongated structural component 400 in order to pivotally connect the first and second elongated structural components 200, 400 to one another.

The coupling component 300 is illustrated as being a rivet in FIGS. 4-8, but the present disclosure is not limited to this configuration. Other pivoting mechanisms may be used to pivotally connect the elongated structural components 200, 400 to one another, for example, a screw, a pin, etc.

Referring to FIGS. 4-8, the first operating portion 250 of the first elongated structural component 200 includes a first end 220 proximate to the through opening of the first elongated structural component 200, a second end 240 distal to the through opening of the first elongated structural component 200, and an elongated body extending between the first and second ends 220, 240.

As illustrated in FIGS. 4-8, the body of the first operating portion 250 may include a first slit 260 penetrating the body entirely in a first direction "A" and extending along at least a portion of a length of the body between the first and second ends 220, 240. For example, when the apparatus 1000 is aligned substantially horizontally, as illustrated in FIG. 4, the first slit 260 may penetrate in a substantially vertical direction "A".

In addition, as illustrated in FIGS. 4-8, the body of the first operating portion 250 may include a second slit 280 penetrating the body entirely in a second direction "B" and extending along at least a portion of the length of the body between the first and second ends 220, 240. The second direction "B" may be different from the first direction "A" and may, for example cross the first direction "A" in a way that the first and second slits 260, 280 intersect one another within the body of the first operating portion 250.

For example, the first and second slits 260, 280 may intersect one another at a right angle within the body of the first operating portion 250. However, this configuration is not limiting, and the first and second slits 260, 280 may also intersect one another at angles other than 90 degrees. For example, when the apparatus 1000 is aligned substantially horizontally, as illustrated in FIG. 4, the second slit 280 may penetrate in a substantially horizontal direction "B".

This configuration, as illustrated in FIGS. 4-8, may define a plurality of holding components 290 in the body of the first operating portion 250. For example, the body of the first operating portion 250 may include four holding components 290, as illustrated in FIGS. 4-8, that are separated from one another along a length direction of the first operating portion 250 (e.g., between the first and second ends 220, 240) due to the presence of the first and second slits 260, 280 therethrough.

The first and second slits 260, 280 may extend through the second end 240 of the body of the first operating portion 250 such that the plurality of holding components 290 are separated from one another at the second end 240 of the body.

Figure 5:
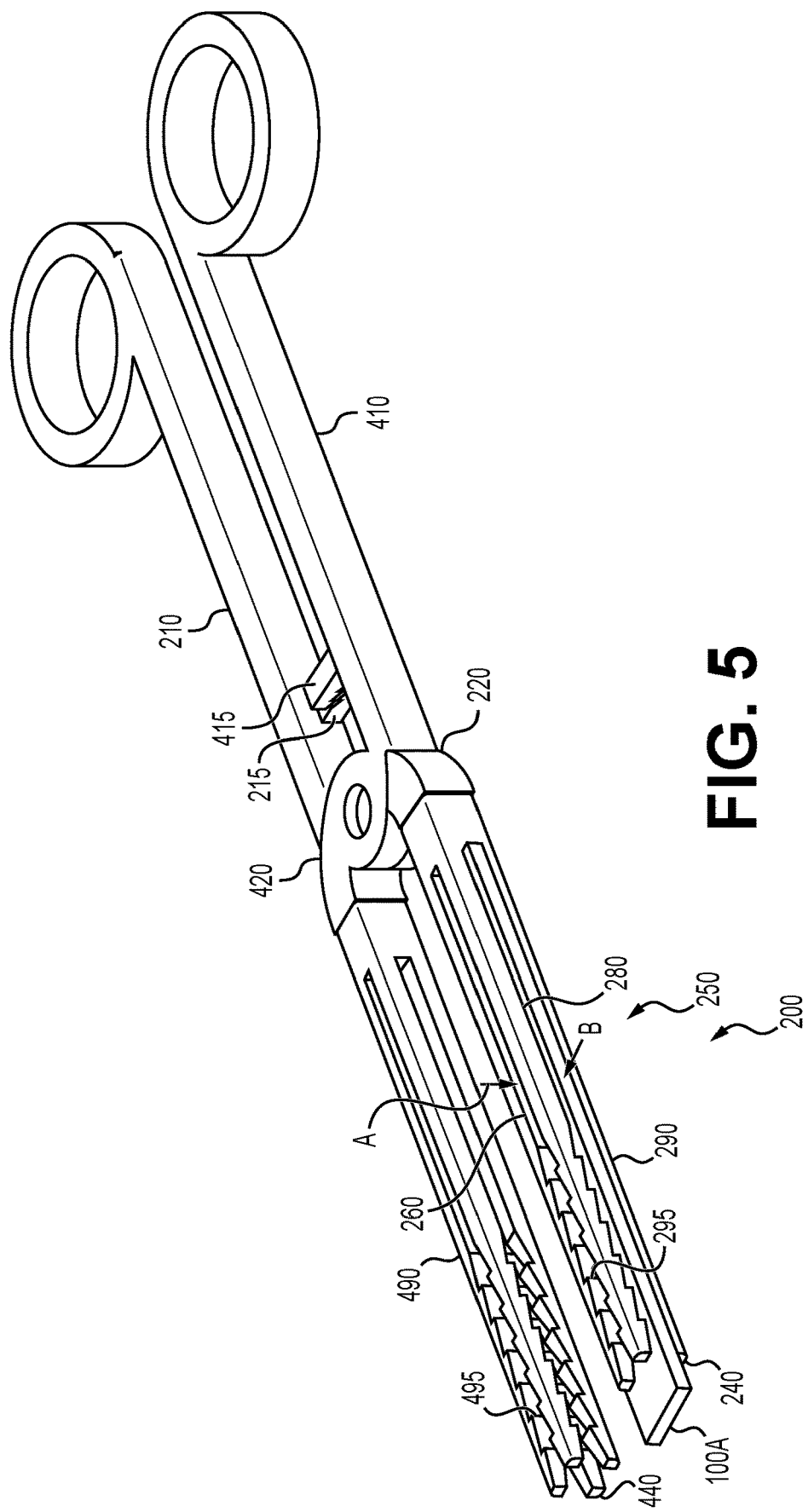
FIG. 5 is a perspective view illustrating the medical device of FIG. 4 loaded with a first type of a nasal pack.

The plurality of holding components 290 of the body of the first operating portion 250 may be configured to hold, for example, a nasal pack 100A that is shaped like a flat bar, as illustrated in FIG. 5. The nasal pack 100A may be similar to the nasal pack 100 described elsewhere in this specification.

The flat bar shaped nasal pack 100A may be inserted in any one of the first and second slits 260, 280, in the body of the first operating portion 250. For example, as illustrated in FIG. 5, the nasal pack 100A may be exemplarily inserted in the second slit 280.

In addition, when the body of the first operating portion 250 is loaded with a flat bar shaped nasal pack 100A in one of the first and second slits 260, 280, as illustrated in FIG. 5, an additional flat bar shaped nasal pack can be inserted (e.g., loaded) in the other slit, from among the first and second slits 260, 280, on either side of the already-inserted nasal pack 100A.

While the body of the first operating portion 250 is described as having a pair of slits (e.g., the first and second slits 260, 280), the present disclosure is not limited to this configuration. For example, the body of the first operating portion 250 may also have a single slit, which would define a pair of holding components in the first operating portion 250, or more than two slits.

Figure 6:
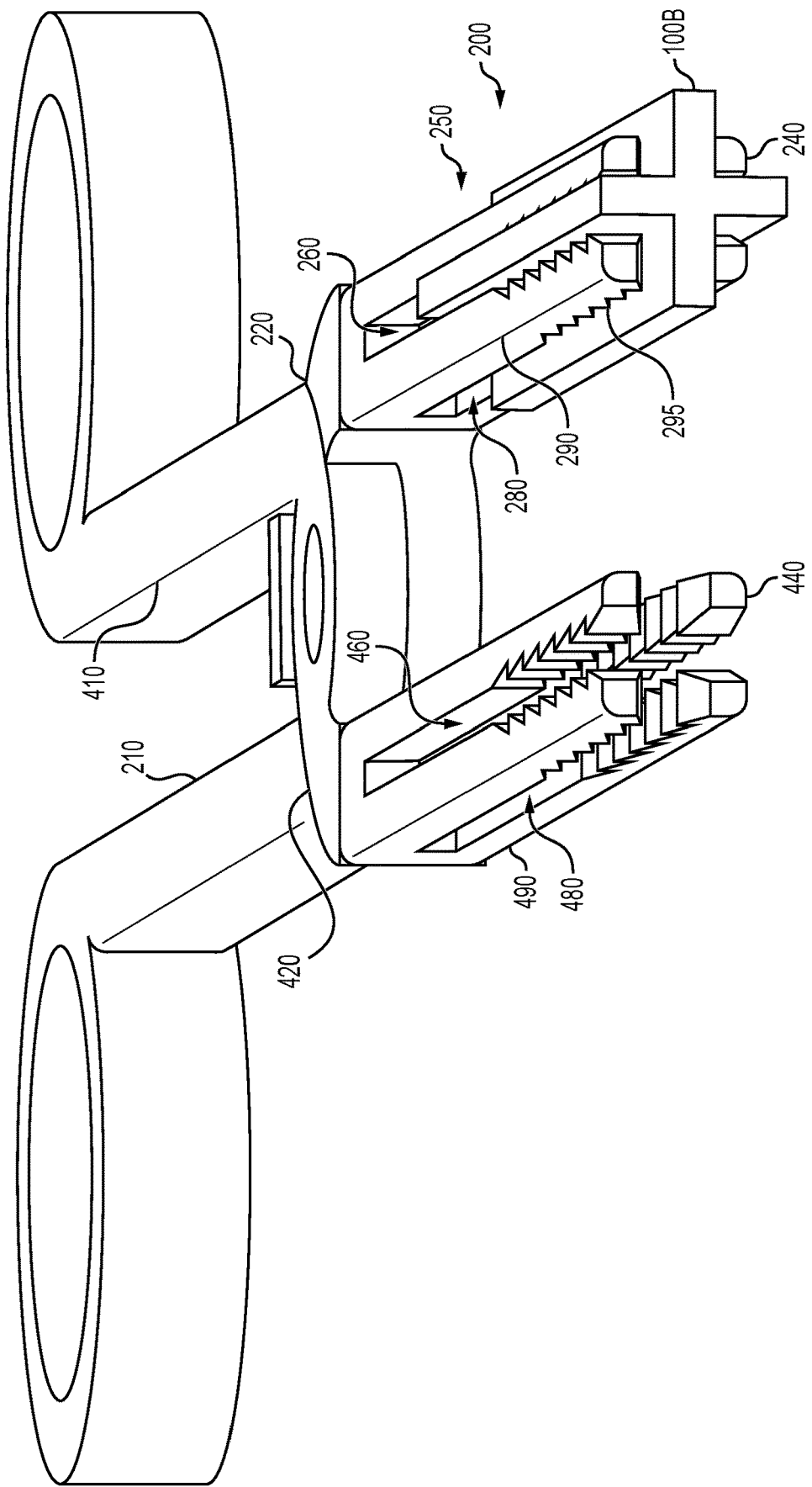
FIG. 6 is a perspective view illustrating the medical device of FIG. 4 loaded with a second type of a nasal pack.

The body of the first operating portion 250 can also be loaded with a cross-shaped or "+"-shaped nasal pack 100B, as illustrated in FIG. 6. For example, the nasal pack 100B of FIG. 6 may have an elongated body with a "+"-shaped cross section that may fit in the first and second slits 260, 280 in the body of the first operating portion 250.

As illustrated in FIGS. 4-8, each one of the holding components 290 of the body of the first operation portion 250 may include a plurality of teeth 295 (or serration/protrusions) disposed adjacent to an area where the first and second slits 260, 280 intersect one another in order to assist with holding the one or more nasal packs loaded in the first operating portion 250 stationary. This configuration may help prevent or significantly reduce slipping of the one or more nasal packs relative to the first operating portion 250 when the first operation portion 250 is loaded with nasal pack(s).

As illustrated in FIGS. 4-8, the teeth 295 of each holding component 290 may extend from the respective holding component at an acute angle, relative to the first end 220 of the body of the first operating portion 250, in order to assist with preventing the nasal pack(s) from moving/sliding toward the second end 240 of the body of the first operating portion 250 (or moving laterally, when using flat bar shaped nasal packs) when one or more nasal pack(s) is/are inserted in the first and/or second slits 260, 280. In other words, the teeth 295 of each holding component 290 may be pointed backwards to prevent the nasal pack(s) from moving once inserted in the first operating portion 250.

The second operating portion 450 of the second elongated structural component 400 may have a similar configuration to that of the first operating portion 250 of the first elongated structural component 200.

For example, as illustrated in FIGS. 4-8, the second operating portion 450 of the second elongated structural component 400 includes a first end 420 proximate to the through opening 490, a second end 440 distal to the through opening 490, and an elongated body extending between the first and second ends 420, 440.

As illustrated in FIGS. 4-8, the body of the second operating portion 450 may include a first slit 460 penetrating the body entirely in a third direction "C" and extending along at least a portion of a length of the body between the first and second ends 420, 440. For example, when the apparatus 1000 is aligned substantially horizontally, as illustrated in FIG. 4, the first slit 460 may penetrate in a substantially vertical direction "C".

In addition, as illustrated in FIGS. 4-8, the body of the second operating portion 450 may include a second slit 480 penetrating the body entirely in a fourth direction "D" and extending along at least a portion of the length of the body between the first and second ends 420, 440. The fourth direction "D" may be different from the third direction "C" and may, for example cross the third direction "C" such that the first and second slits 460, 480 may intersect one another within the body of the second operating portion 450. For example, the first and second slits 460, 480 may intersect one another at a right angle within the body of the second operating portion 450. However, this configuration is not limiting, and the first and second slits 460, 480 may also intersect one another at angles other than 90 degrees. For example, when the apparatus 1000 is aligned substantially horizontally, as illustrated in FIG. 4, the second slit 480 may penetrate in a substantially horizontal direction "D".

This configuration, as illustrated in FIGS. 4-8, may define a plurality of holding components 490 in the body of the second operating portion 450. For example, the body of the second operating portion 450 may include four holding components 490 due to the presence of the first and second slits 460, 480.

The first and second slits 460, 480 may extend through the second end 440 of the body of the second operating portion 450 such that the plurality of holding components 490 would be separated from one another at the second end 440 of the body.

The second operating portion 450 may be loaded with one or more nasal packs as described in this specification with reference to the first operating portion 250. In addition, it is understood that either one of the first and second operating portions 250, 450 can be loaded with one or more nasal packs as described in this specification, or both the first and second operating portions 250, 450 can be loaded with one or more nasal packs each, as described in this specification.

The second operating portion 450 may also be modified to have a single slit, as described in this specification with reference to the first operating portion 250.

As illustrated in FIGS. 4-8, each one of the holding components 490 of the body of the second operation portion 450 may include a plurality of teeth 495 (or serration/protrusions) disposed adjacent to an area where the first and second slits 460, 480 intersect one another in order to assist with holding the one or more nasal packs loaded in the second operating portion 450 stationary. The teeth 495 of the holding components 490 of the body of the second operating portion 450 may be configured similarly to the teeth 295 of the holding components 290 of the body of the first operating portion 250.

Figure 3:
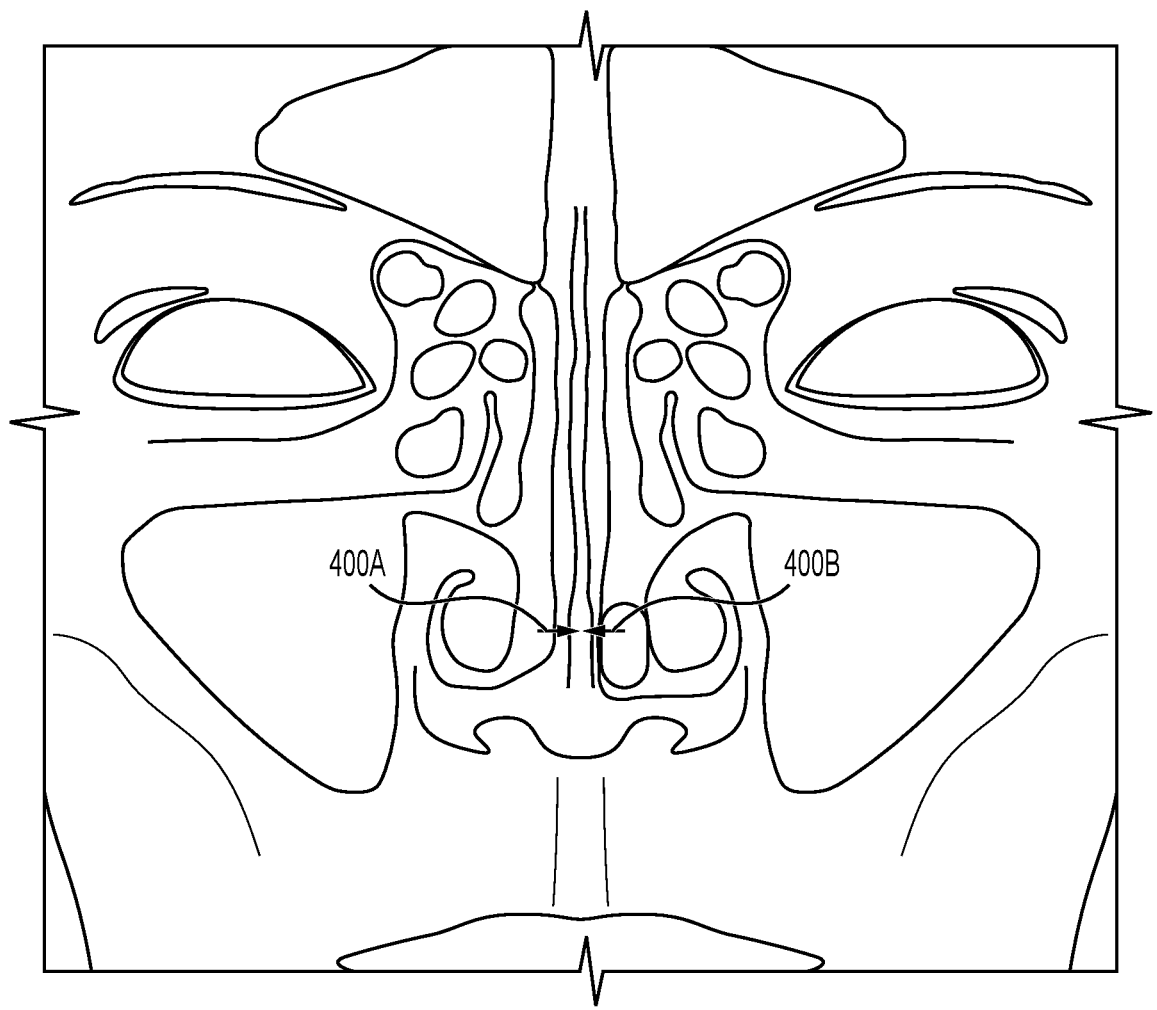
FIG. 3 is a front view diagram illustrating the anatomy of the human nose.
Figure 7:
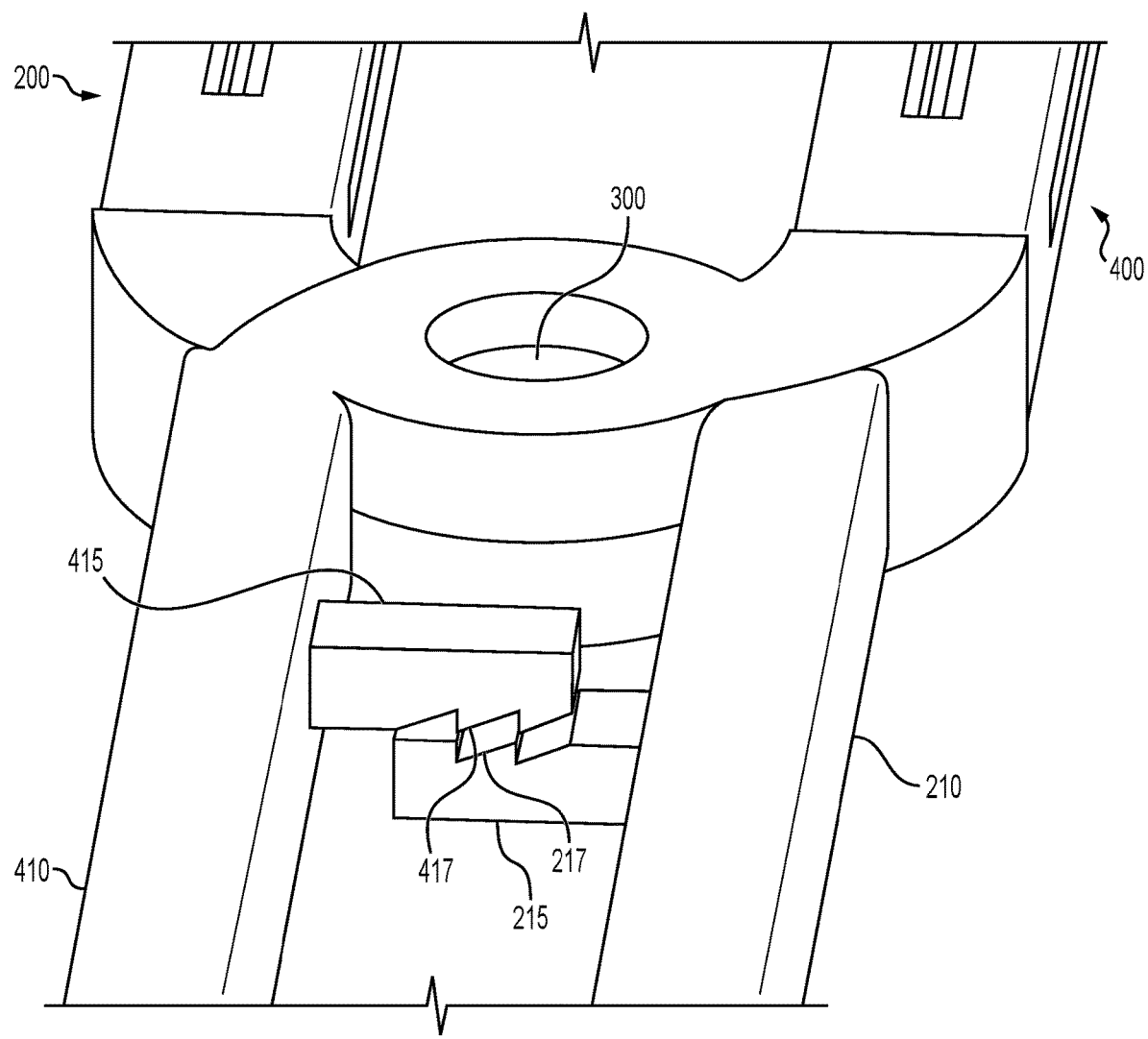
FIG. 7 is a perspective view illustrating the medical device of FIG. 4.
Figure 8:
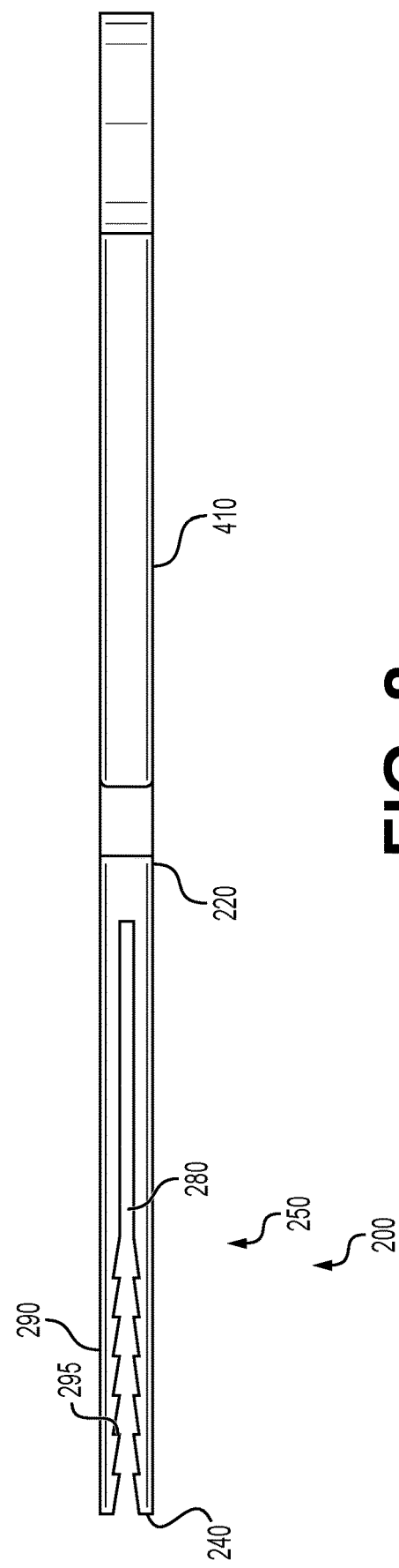
FIG. 8 is a side view illustrating the medical device of FIG. 4.

As more clearly illustrated in FIGS. 4, 5 and 7, the first elongated structural component 200 may include a first elongated locking bar 215 protruding from the first handle portion 210 in a direction toward the second handle portion 410 when the apparatus 1000 is in the closed state (or nearly the closed state), as illustrated in FIGS. 3, 4 and 7. The first elongated locking bar 215 may include a plurality of teeth 217 formed along its length.

"Near" the closed state, in this case, means a state in which the first and second elongated structural components 200, 400 are positioned (or pivoted) relative to one another in a state that enables the first and second handle portions 210, 410 to be moved (e.g., squeezed or pressed) toward one another by a certain amount (or degree) to bring the first and second operating portions 250, 450 closer together before the first and second handle portions 210, 410 can no longer be moved closer to one another. In other words, "near" the closed state means a state in which the first and second handle portions 210, 410 can still be brought closer to one another.

In addition, the second elongated structural component 400 may include a second elongated locking bar 415 protruding from the second handle portion 410 in a direction toward the first handle portion 210 when the apparatus 1000 is in the closed state (or nearly the closed state), as illustrated in FIGS. 3, 4 and 7. The second elongated locking bar 415 may include a plurality of teeth 417 formed along its length.

As more clearly illustrated in FIG. 7, the first and second elongated locking bars 215, 415 are configured to overlap one another when the apparatus 1000 is in the closed state and near the closed state such that the teeth 217, 417 thereof can be selectively engaged with one another to selectively lock the first and second elongated structural components 200, 400 at different positions relative to one another.

The closed or near closed states of the apparatus 1000 may be the states in which the apparatus 1000 is intended to be operated (e.g., with the first and second elongated structural components 200, 400 are loaded with nasal packs(s) and are inserted in a patient's nose) such that the inserted nasal pack(s) can apply pressure to a bleeding site in the nasal cavities of the patient to stop or control the bleeding.

For example, when the nasal pack(s) held by the first and second operating portions 250 and 450 have been inflated inside of the nose, the handle portions 210 and 410 can be manipulated (e.g., squeezed toward one another) in order to gradually increase the pressure that the nasal packs apply to a bleeding site inside of the nose (e.g., to Little's area) until the bleeding is controlled or stopped.

The first and second locking bars 215, 217 can be utilized to selectively lock the first and second elongated structural components 200 and 400 in this position such that a physician would not have to continuously apply pressure to the first and second handle portions 210, 410 by hand in order to maintain pressure on the bleeding site. This feature of the apparatus 1000, in combination with the structural configuration of the apparatus 1000 as described in this specification, helps to direct pressure (via the nasal packs) to a nasal bleeding site (e.g., to Little's area), as illustrated by arrows 400A, 400B in FIG. 3, rather than unnecessary applying pressure on the nasal floor and the inferior turbinate.

The length of the first and second elongated locking bars 215, 415 and/or the number of teeth 217, 417 included in each respective elongated locking bar 215, 415 may be varied as needed such that the first and second operating portions 250 and 450 can be selectively locked at different positions (or angles) relative to one another to accommodate the anatomy of different patients.

In addition, the size of the first and second operating portions 250 and 450, including the size of each component thereof as described in this specification, can be varied to accommodate the anatomy of different patients in a way that enables the nasal pack(s) to expand outwardly from their respective first and second slits to apply pressure to a bleeding site inside of the nose while enabling the patient to breathe through the nose.

The first and second operating portions 250, 450, loaded with nasal pack(s), may enable a patient to breathe through the nose because the plurality of holding components 290, 490, respectively, of the body of the first and second operating portions 250, 450 may prevent the loaded nasal pack(s) from expanding outwardly through the holding components 290, 490 (although a negligible degree of bending outwardly of the holding components 290, 490 may occur due to the outwardly pressure exerted thereon by the inflated nasal pack(s)). This configuration enables an air passageway to be maintained between the holding components 290, 490, respectively, of the body of the operating portion 250, 450, and the nasal cavity of a patient, thereby enabling a patient to breathe through the nose.

In addition, the apparatus 1000 may be configured such that the first end 220 of the first operating portion 250 and the first end 420 of the second operating portion 450 are spaced apart from one another when the medical apparatus is in a closed state or near the closed state, as illustrated in FIGS. 4-7, for comfort purposes, for example, to account for the septum.

While the dimensions of the first and second elongated structural components 200, 400 can be varied as needed, by taking into consideration the anatomy of a patient and to provide a comfortable grip to an operating physician, in a non-limiting configuration, the first and second operating portions 250, 450 may be about 8 cm long each, and the first and second handle portions 210, 410 may be about 7 cm long each.

A method of operating the apparatus 1000 may include obtaining the apparatus 1000, obtaining one or more nasal packs, coupling each one of the operating portions 250, 450 of the medical apparatus 1000 with one or more of the obtained nasal packs, inserting the first and second operating portions 250, 450, respectively, in the first and second nasal cavities of a patient, and inflating the nasal pack(s) loaded in each of the first and second operating portions 250, 450 once said portions 250, 450 are inserted in the patient's nose. The inflation of the nasal pack(s) may be carried out by, for example, injecting the nasal pack(s) with a fluid, for example, saline, by irrigating the nose, etc.

The first and second handle portions 210, 410 may be pressed toward one another until the bleeding is controlled or stops, and the locking bars 215, 415 may be selectively engaged with one another at this position to lock the first and second operating portions 250, 450 in place. This configuration enables the apparatus 1000 to control or stop the bleeding by continuously applying pressure to a bleeding site inside of the nose while enabling the patient to breathe through the nose in relative comfort.

When the epistaxis has been managed, for example, when the bleeding stops, the locking bars 215, 415 may be selectively disengaged from one another and the first and second operating portions 250, 450 may be withdrawn from the patient's nose.

The device 1000 may be used, for example, with one nasal pack loaded in either one of the operating portions 250, 450, whether the nasal pack is flat bar shaped or "+"-shaped, with more than one nasal pack inserted in either one of the operating portions 250, 450, or with one or more nasal packs in each one of the operating portions 250, 450.

While the present disclosure has been particularly shown and described with reference to exemplary embodiments thereof, it will be apparent to those of ordinary skill in the art that various changes in form and detail may be made therein without departing from the spirit and scope of the present disclosure as defined by the following claims.

What is claimed is:

1. A medical apparatus, comprising:
a first elongated structural component;
a second elongated structural component; and
a coupling component pivotally coupling the first and second elongated structural components to one another,
wherein the first elongated structural component includes a first handle portion, a first operating portion and a first through opening disposed between the first handle portion and the first operating portion,
wherein the second elongated structural component includes a second handle portion, a second operating portion and a second through opening disposed between the second handle portion and the second operating portion,
wherein the coupling component extends at least partially in the first and second through openings, and
wherein the first operating portion has a first end proximate to the first through opening, a second end distal to the first through opening, and a body extending between the first and second ends thereof, wherein the body of the first operating portion includes a first slit penetrating said body entirely in a first direction and extending along at least a portion of a length of said body between the first and second ends thereof, the first slit defining a first holding component and a second holding component in the body of the first operating portion,
wherein the body of the first operating portion further includes a second slit penetrating said body entirely in a second direction, wherein the second slit extends along at least a portion of the length of said body between the first and second ends thereof, wherein the second direction is different from the first direction such that the first and second slits intersect one another in the body of the first operating portion,
wherein the first and second slits define the first holding component, the second holding component, a third holding component and a fourth holding component in the body of the first operating portion,
wherein the first holding component, the second holding component, the third holding component and the fourth holding component extend along a same portion of the length of the body of the first operating portion, said same portion of the length of the body of the first operating portion extending in a direction between the first and second ends of said body, and
wherein the first holding component, the second holding component, the third holding component and the fourth holding component are separated from one another by the first and second slits along respective lengths of the first holding component, the second holding component, the third holding component and the fourth holding component, said respective lengths of said first to fourth holding components extending in the direction between the first and second ends of the body of the first operating portion.

2. The medical apparatus of claim 1, wherein the first slit extends through the second end of the body of the first operating portion such that the first and second holding components are separated from one another at the second end of the body of the first operating portion.

3. The medical apparatus of claim 2, wherein the second slit extends through the second end of the body of the first operating portion such that the first holding component, the second holding component, the third holding component and the fourth holding component are separated from one another at the second end of the body of the first operating portion.

4. The medical apparatus of claim 1, wherein at least one of the first and second holding components includes teeth along its respective length.

5. The medical apparatus of claim 4, wherein the teeth are disposed adjacent to the first slit, and are configured to assist in preventing a nasal pack, insertable in the first slit, from moving when the nasal pack is inserted in the first slit.

6. The medical apparatus of claim 5, wherein the teeth extend from the first holding component at an acute angle, relative to the first end of the body of the first operating portion, in order to assist in preventing the nasal pack from moving toward the second end of the body of the first holding component when the nasal pack is inserted in the first slit.

7. The medical apparatus of claim 1, wherein each one of the first holding component, the second holding component, the third holding component and the fourth holding component has teeth disposed adjacent to an area where the first and second slits intersect one another.

8. The medical apparatus of claim 1, wherein the second operating portion has a first end proximate to the second through opening, a second end distal to the second through opening, and a second body extending between the first and second ends thereof, wherein the second body of the second operating portion includes a first slit penetrating said second body entirely in a third direction and extending along at least a portion of a length of said second body between the first and second ends thereof, the first slit defining a first holding component and a second holding component in the second body.

9. The medical apparatus of claim 8, wherein the second body further includes a second slit penetrating said second body entirely in a fourth direction, wherein the second slit extends along at least a portion of the length of said second body between the first and second ends thereof,
wherein the fourth direction is different from the third direction such that the first and second slits intersect one another in the second body, and wherein the first and second slits define the first holding component, the second holding component, a third holding component and a fourth holding component in the second body.

10. The medical apparatus of claim 9, wherein the first and second slits of the second body extend through the second end of the second body such that the first holding component, the second holding component, the third holding component and the fourth holding component of the second body are separated from one another at the second end of the second body.

11. The medical apparatus of claim 1, wherein the first end of the first operating portion and the first end of the second operating portion are spaced apart from one another when the medical apparatus is in a closed state or near the closed state.

12. The medical apparatus of claim 1, wherein at least one selected from the group consisting of the first and second elongated structural components includes a metal.

13. The medical apparatus of claim 12, wherein the metal is selected from the group consisting of stainless steel, titanium, nickel and chromium.

14. The medical apparatus of claim 1, wherein the first elongated structural component further includes a first elongated locking bar extending from the first handle portion and the second elongated structural component further includes a second elongated locking bar extending from the second handle portion,
wherein the first and second elongated locking bars are configured to overlap with one another and to be selectively locked to one another along different portions of their respective lengths in order to selectively lock the first and second operating portions at different positions relative to one another.

15. A medical apparatus, comprising:
a first elongated structural component;
a second elongated structural component;
a coupling component pivotally coupling the first and second elongated structural components to one another,
wherein the first elongated structural component includes a first handle portion, a first operating portion and a first through opening disposed between the first handle portion and the first operating portion,
wherein the second elongated structural component includes a second handle portion, a second operating portion and a second through opening disposed between the second handle portion and the second operating portion,
wherein the coupling component extends at least partially in the first and second through openings, and
wherein the first operating portion has a first end proximate to the first through opening, a second end distal to the first through opening, and a body extending between the first and second ends thereof, wherein the body of the first operating portion includes a first slit penetrating said body entirely in a first direction and extending along at least a portion of a length of said body between the first and second ends thereof, the first slit defining a first holding component and a second holding component in the body of the first operating portion,
wherein the body of the first operating portion further includes a second slit penetrating said body entirely in a second direction, wherein the second slit extends along at least a portion of the length of said body between the first and second ends thereof, wherein the second direction is different from the first direction such that the first and second slits intersect one another in the body of the first operating portion,
wherein the first and second slits define the first holding component, the second holding component, a third holding component and a fourth holding component in the body of the first operating portion,
wherein the first holding component, the second holding component, the third holding component and the fourth holding component extend along a same portion of the length of the body of the first operating portion, said same portion of the length of the body of the first operating portion extending in a direction between the first and second ends of said body, and wherein the first holding component, the second holding component, the third holding component and the fourth holding component are separated from one another by the first and second slits along respective lengths of the first holding component, the second holding component, the third holding component and the fourth holding component, said respective lengths of said first to fourth holding components extending in the direction between the first and second ends of the body of the first operating portion; and a nasal pack disposed in the first slit, said nasal pack extending in the first slit along the same portion of the length of the body of the first operating portion where the first holding component, the second holding component, the third holding component and the fourth holding component extend.

16. The medical apparatus of claim 15, wherein the nasal pack has a flat bar shape.

17. The medical apparatus of claim 15, wherein the nasal pack has a cross-shape or a "+"-shape, wherein the nasal pack extends in the first slit and in the second slit along the same portion of the length of the body of the first operating portion where the first holding component, the second holding component, the third holding component and the fourth holding component extend.

18. The medical apparatus of claim 17, wherein the wherein the first slit extends through the second end of the body of the first operating portion and the second slit extends through the second end of the body of the first operating portion such that the first holding component, the second holding component, the third holding component and the fourth holding component are separated from one another at the second end of the body of the first operating portion.

* * * * *